United States Patent [19]

Boussignac

[11] Patent Number: 5,452,715
[45] Date of Patent: Sep. 26, 1995

[54] TUBE FOR ASSISTING BREATHING

[76] Inventor: Georges Boussignac, 1 Avenue de Provence, 92160 Antony, France

[21] Appl. No.: 175,123

[22] Filed: Dec. 29, 1993

[30] Foreign Application Priority Data

Aug. 26, 1993 [FR] France .................................. 93 10264

[51] Int. Cl.$^6$ ................................................. A61M 16/00
[52] U.S. Cl. .................................. 128/207.15; 128/207.14
[58] Field of Search ............................. 128/207.14, 207.15, 128/207.16; 604/101, 102

[56] References Cited

U.S. PATENT DOCUMENTS

| | | | |
|---|---|---|---|
| 2,791,217 | 5/1957 | Iskander | 128/203 |
| 3,173,418 | 3/1965 | Baran | 604/101 |
| 3,211,152 | 10/1965 | Stern | 604/101 |
| 3,437,747 | 4/1969 | Sheldon | 178/6 |
| 3,707,151 | 12/1972 | Jackson | 128/351 |
| 3,821,570 | 6/1974 | Burson | 310/70 |
| 3,859,995 | 1/1975 | Colston . | |
| 3,881,479 | 5/1975 | Carden | 128/145.8 |
| 3,915,173 | 10/1975 | Brekke | 128/351 |
| 3,982,541 | 9/1976 | L'Esperance, Jr. | 128/6 |
| 3,991,764 | 11/1976 | Incropera et al. | 128/303.1 |
| 4,176,662 | 12/1979 | Frazer | 128/6 |
| 4,183,102 | 1/1980 | Guiset | 3/1.4 |
| 4,265,237 | 5/1981 | Schwanbom et al. | 128/204.24 |
| 4,270,530 | 6/1981 | Baum et al. | 128/204.25 |
| 4,289,128 | 9/1981 | Rüsch | 128/207.15 |
| 4,299,237 | 11/1981 | Foti | 128/742 |
| 4,418,688 | 12/1983 | Loeb | 128/6 |
| 4,423,725 | 1/1984 | Daran et al. | 128/200.26 |
| 4,470,407 | 9/1984 | Hussein | 128/6 |

(List continued on next page.)

FOREIGN PATENT DOCUMENTS

| | | |
|---|---|---|
| 0074809 | 3/1983 | European Pat. Off. . |
| 0112668 | 7/1984 | European Pat. Off. . |
| 0152694 | 8/1985 | European Pat. Off. . |
| 0153991 | 9/1985 | European Pat. Off. . |
| 0245142 | 11/1987 | European Pat. Off. . |
| 2613639 | 10/1988 | France . |
| 160709 | 6/1903 | Germany . |
| 2353153 | 4/1975 | Germany . |
| 1171439 | 11/1969 | United Kingdom . |

OTHER PUBLICATIONS

Boussignac, G. et al., "Efficiency of an Endotracheal New Set Up Allowing A Continuous Additional Gas Flow" Departement D'Anesthesie–Reanimation, Hospital H. Mondor, 94010 Cretail, 13 pages.
International (PCT) Publication No. WO84/01513.
International (PCT) Publication No. WO88/00071.
International (PCT) Publication No. WO85/02101.
Trang et al., Intensive Care Medicine. 13(6), No. 65, 1987, (Abstract).
Trang et al., Intensive Care Medicine. 13(6), No. 100, 1987, (Abstract).
Boussignac et al., Neonatal Respiration. No. 1150, (Abstract).
International (PCT) Published Patent Document No. WO89/06983.
International (PCT) Published Patent Document No. WO90/11972.
Mion et al., ASA Congress in San Francisco, Oct. 1988, (Abstract).

(List continued on next page.)

Primary Examiner—Edgar S. Burr
Assistant Examiner—Aaron J. Lewis
Attorney, Agent, or Firm—Fisher, Christen & Sabol

[57] ABSTRACT

A breathing-assistance tube whose distal end is designed to be inserted into the trachea of a patient and is provided with an inflatable balloon for providing sealing between said breathing-assistance tube and said trachea, has a proximal end for connection to means for conveying breathing gas into the lungs of the patient via said tube. According to the invention, said breathing-assistance tube includes at least one communication duct passing through the wall of said tube and establishing communication between the lumen of said tube and the inside of said balloon.

10 Claims, 3 Drawing Sheets

U.S. PATENT DOCUMENTS

| | | | |
|---|---|---|---|
| 4,520,812 | 6/1985 | Freitag et al. | 128/204.25 |
| 4,573,462 | 3/1986 | Baum | 128/204.25 |
| 4,581,017 | 4/1986 | Sahota | 604/101 |
| 4,584,998 | 4/1986 | McGrail | 128/604 |
| 4,592,353 | 6/1986 | Daikuzono | 128/303.1 |
| 4,612,929 | 9/1986 | Schübert et al. | 128/204.25 |
| 4,657,014 | 4/1987 | Edelman et al. | 128/303.1 |
| 4,694,828 | 9/1987 | Eichenbaum | 128/303.1 |
| 4,739,756 | 6/1988 | Horn | 128/207.14 |
| 4,751,924 | 6/1988 | Hammerschmidt et al. | 128/207.15 |
| 4,762,129 | 8/1988 | Bonzel | 128/344 |
| 4,821,714 | 4/1989 | Smelser | 604/102 |
| 4,825,862 | 5/1989 | Sato et al. | 128/207.15 |
| 4,832,024 | 5/1989 | Boussignac et al. | 128/303.1 |
| 4,872,483 | 10/1989 | Shah | 128/207.15 |
| 4,976,261 | 12/1990 | Gluck et al. | 604/102 |
| 5,000,734 | 3/1991 | Boussignac et al. | 604/96 |
| 5,036,847 | 8/1991 | Boussignac et al. | 128/207.14 |
| 5,235,973 | 8/1993 | Levinson | 128/207.15 |
| 5,304,135 | 4/1994 | Shonk | 604/101 |
| 5,318,021 | 6/1994 | Alessi | 128/207.15 |

OTHER PUBLICATIONS

Isabey et al., Mechanics of Breathing II: Airways, Abstract No. 1129.

Isabey et al., "Effect of Air Entrainment on Airway Pressure During Endotrachael Gas Injection," presented in part at the 711st annual mtg. at the FASEB in Washington, D.C., Mar. 29–Apr. 2, 1987.

Isabey et al., "Mecanisme de L'Entrainement D'Air Induit Par Des Microjets Gazeux, Dans Une Sonde D'Intubation", J. de Biophys. et B., vol. 11, (1987), suppl. No. 1, pp. 80 and 81.

L. Brochard et al., "Constant Flow In Sufflation Prevents Arterial Oxygen Desaturation During Ventilator Disconnection:", Reanimation Medicale, Hospital Henre Mondor, Cretail Cedex, France, 25 pages.

L. Beydon et al., "Mechanical Ventilation Without A Ventilator: Utilisation Of The Properties Of A New Intubation Tube", (Abstract).

L. Beydon et al., "Testing Of A New Intubation Tube For Inspiratory Assistance", (Abstract).

TUBE FOR ASSISTING BREATHING

The present invention relates to a tube for assisting breathing, for use with patients whose spontaneous breathing is absent or insufficient.

BACKGROUND OF THE INVENTION

Apparatuses for assisted breathing are already known that comprise means for conveying a breathing gas into the lungs of a patient and, optionally, for removing said gas, via a breathing-assistance tube or probe whose distal end is generally designed to be inserted into the trachea of the patient. Under such circumstances, it is common practice to provide an inflatable balloon at the distal end of the tube for the purpose of sealing the tube to the trachea. The balloon is inserted into the trachea while in the deflated state, and it is then inflated once it has been installed therein. To inflate the balloon, an inflation gas generator is provided at the proximal end of the tube and is generally incorporated in the breathing gas generator. The inflation pressure of the balloon is determined independently of the pressure of breathing gas insufflated into the lungs of the patient, and in such a manner that the balloon bears continuously against the walls of the trachea and gives rise to sufficient sealing between the breathing-assistance tube and the trachea.

In spite of all the precautions that can be taken, such as limiting inflation pressure to the smallest value compatible with essential sealing, the thrust pressure exerted by the balloon against the walls of the trachea is traumatic therefor. This can give rise to severe consequences for the patient, such as necrosis of the tissue of the walls of the trachea.

OBJECTS AND SUMMARY OF THE INVENTION

An object of the present invention is to remedy that drawback and to make it possible to eliminate, or at least greatly reduce, tracheal traumatism due to the inflatable balloon of a breathing-assistance tube inserted into a trachea.

To this end, according to the invention, a breathing-assistance tube whose distal end is designed to be inserted into the trachea of a patient and is provided with an inflatable balloon for providing sealing between said breathing-assistance tube and said trachea, and whose proximal end is designed to be connected to means for conveying breathing gas to the lungs of the patient via said tube, is remarkable in that it includes at least one communication duct passing through the wall of said tube and establishing communication between the lumen of said tube and the inside of said balloon.

Thus, since the gas generator for inflating the balloon is omitted, the balloon in place in the trachea is inflated and deflated at the same rate as breathing gas is insufflated. The thrust pressure exerted by the balloon against the walls of the trachea is thus no longer continuous, but is cyclical. Furthermore, the inflation pressure of the balloon is equal to the pressure of the breathing gas which, by definition, is chosen to be non-traumatic for the lungs of the patient. Because of those two observations, it can be seen that the inflatable balloon of the invention cannot traumatize the wall of the trachea.

Furthermore, it will be observed that although the breathing-assistance tube of the invention provides sealing with the trachea that is not continuous but that is cyclical, no disadvantage stems therefrom since the sealing portion of the cycle takes place specifically while breathing gas is being passed into the lungs, thereby ensuring that the breathing gas does not escape to the outside.

Preferably, in order to remove any mucous that may be deposited on the balloon, said communication duct is located in the vicinity of the most distal end of the balloon. In this respect, it is also advantageous for said communication duct to be inclined relative to said tube, the orifice through which said communication duct opens out into the lumen of said tube being closer to the distal end face thereof than is the orifice whereby said communication duct opens out into said balloon.

In order to ensure maximum safety, said tube advantageously includes at least one first longitudinal duct in the thickness of its wall and opening out into the cavity of said balloon, said duct being designed to be connected to a pressure sensor suitable for monitoring the operation of said means delivering the breathing gas to the lungs of the patient. Preferably, said first longitudinal duct opens out into the cavity of said balloon in the vicinity of the less distal end thereof.

Said inflatable balloon may be subdivided into two cavities, said communication duct opening out into one of said cavities and a second longitudinal duct formed in the thickness of said tube opening out into the other one of said cavities, the second longitudinal duct being suitable for connection to a source of gas at low pressure. It is thus possible to impart a residual shape to said balloon that is not completely flattened when the balloon is deflated. In which case, said first longitudinal duct for connection to said pressure sensor opens out into the same cavity as said communication duct.

In known manner, the breathing-assistance tube may include internal deflection means for at least one jet of breathing gas conveyed by a third longitudinal duct formed in the thickness of said tube.

In which case, said tube includes another through duct connecting the cavity of said balloon with the portion of said lumen of said tube lying between said internal deflection means and the distal end face of said tube.

If the balloon includes two cavities in the manner described above, said other through duct opens out into the same cavity as said communication duct.

BRIEF DESCRIPTION OF THE DRAWINGS

The figures of the accompanying drawings make it easy to understand how the invention can be implemented. In the figures, identical references designate elements that are similar.

MORE DETAILED DESCRIPTION

Figure 1:
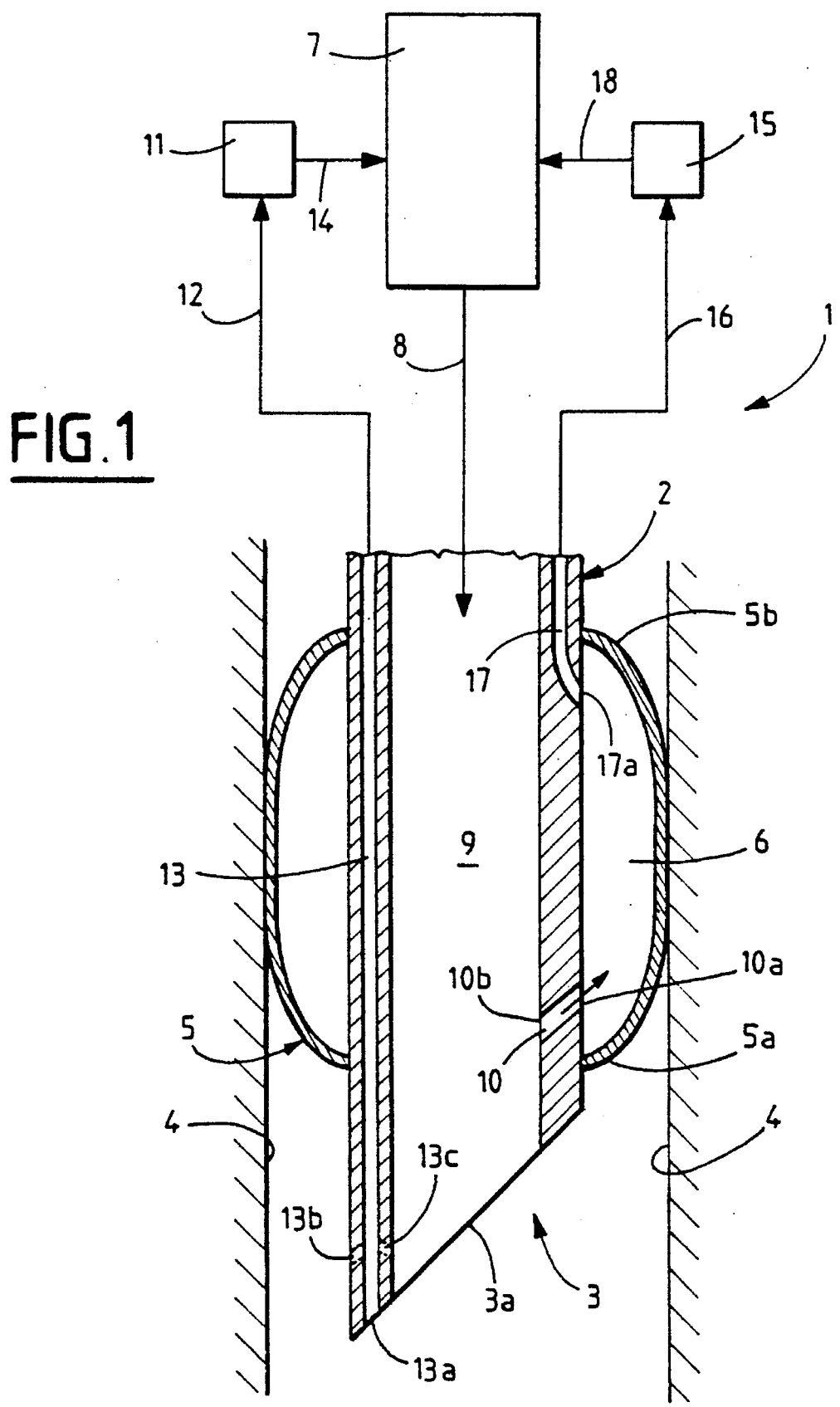
FIGS. 1 to 3 are block diagrams of variant embodiments of breathing-assistance tubes of the invention in place in a trachea. These figures, show only the distal portion of each of said tubes (on a large scale) plus an associated artificial ventilator (as a block diagram).

The breathing-assistance apparatus 1 shown in FIG. 1 comprises a breathing-assistance tube 2 of the present invention whose distal end 3 for insertion into the trachea 4 of a patient is provided with an inflatable balloon 5 defining a closed cavity 6 around said tube 2. The balloon 5 is in the deflated state when it is inserted into the trachea 4, and once it is in place therein, its main purpose in the inflated state is to provide sealed closure of the annular space between the distal end 3 of the tube 2 and the trachea 4 so as to prevent any uncontrolled return of breathing gas out from the patient when said gas is inserted into the lungs of the patient via said tube 2.

An artificial ventilator 7 is provided to insufflate a breathing gas under cyclic pressure into said lungs (not shown but disposed towards the bottom of FIG. 1). Such a breathing gas may be oxygen, or a mixture of gases containing oxygen, and it may be insufflated with a peak pressure equal to 3 bars, for example. The ventilator 7 operates periods of insufflation (and optionally periods of breathing out) to assist the breathing of the patient. It is connected by means of a link 8 to the lumen 9 of said breathing-assistance tube 2.

In accordance with the present invention, said lumen 9 of the breathing-assistance tube 2 is in communication with the inside cavity 6 of the balloon 5 via at least one through duct 10 passing through the wall of the distal end portion 3 of the tube 2. The duct 10 is preferably adjacent to the most distal end 5a of the balloon 5 and is inclined so that its orifice 10b through which it opens out into the lumen 9 of the tube 2 is closer to the end face 3a of the distal end 3 of said tube than is its orifice 10a through which it opens out into the cavity 6 of the balloon 5.

For safety reasons, means may be provided to interrupt the operation of the ventilator in the event of excess pressure. For example, in the embodiment of FIG. 1, the following are provided:

- a first pressure sensor 11 connected via a link 12 to a longitudinal capillary duct 13 formed in the thickness of the wall of the tube 2 and opening out downstream from the balloon 5, e.g. at 13a in the end face 3a, and/or at 13b and at 13c in the inside and outside walls of said tube 2. The first pressure sensor 11 is suitable, via a link 14, for interrupting operation of the ventilator 7; and
- a second pressure sensor 15 connected by a link 16 to a longitudinal capillary duct 17 received in the thickness of the wall of the tube 2 and opening out at 17a into the cavity 6 of the balloon 5, preferably adjacent to the less distal end 5b thereof. The second pressure sensor 15 is suitable, via a link 18, for interrupting operation of the ventilator 7.

Thus, when the ventilator 7 is switched on after the breathing-assistance tube 2 has been inserted in the trachea 4 with the balloon 5 in the deflated state, the ventilator causes breathing gas to be passed at a pressure that varies cyclically at the desired insufflation rate into the lumen 9 of the tube 2 leading to the lungs of the patient. Because of the through duct 10, the pressure inside the cavity 6 of the balloon 5 is continuously equal to the pressure that obtains inside said lumen 9. Consequently, the balloon 5 is inflated and deflated at the rate at which the pressure varies in the breathing gas passed by the ventilator 7 into the tube 2. The balloon 5 thus provides sealing within the trachea 4 whenever breathing gas passes along the tube 2 towards the lungs. In contrast, in the absence of breathing gas in the tube 2, the balloon 5 deflates.

Thus, the continuous pressure as exerted against the trachea by the balloons of known breathing-assistance tubes is avoided, which continuous pressure can traumatize the trachea.

It will be observed that the maximum pressure accepted in the balloon 5 is the peak pressure of the breathing gas, and since said peak pressure is naturally chosen to avoid trauma of the lungs, it is a fortiori incapable of damaging the trachea when it presses the balloon 5 thereagainst.

Figure 2:
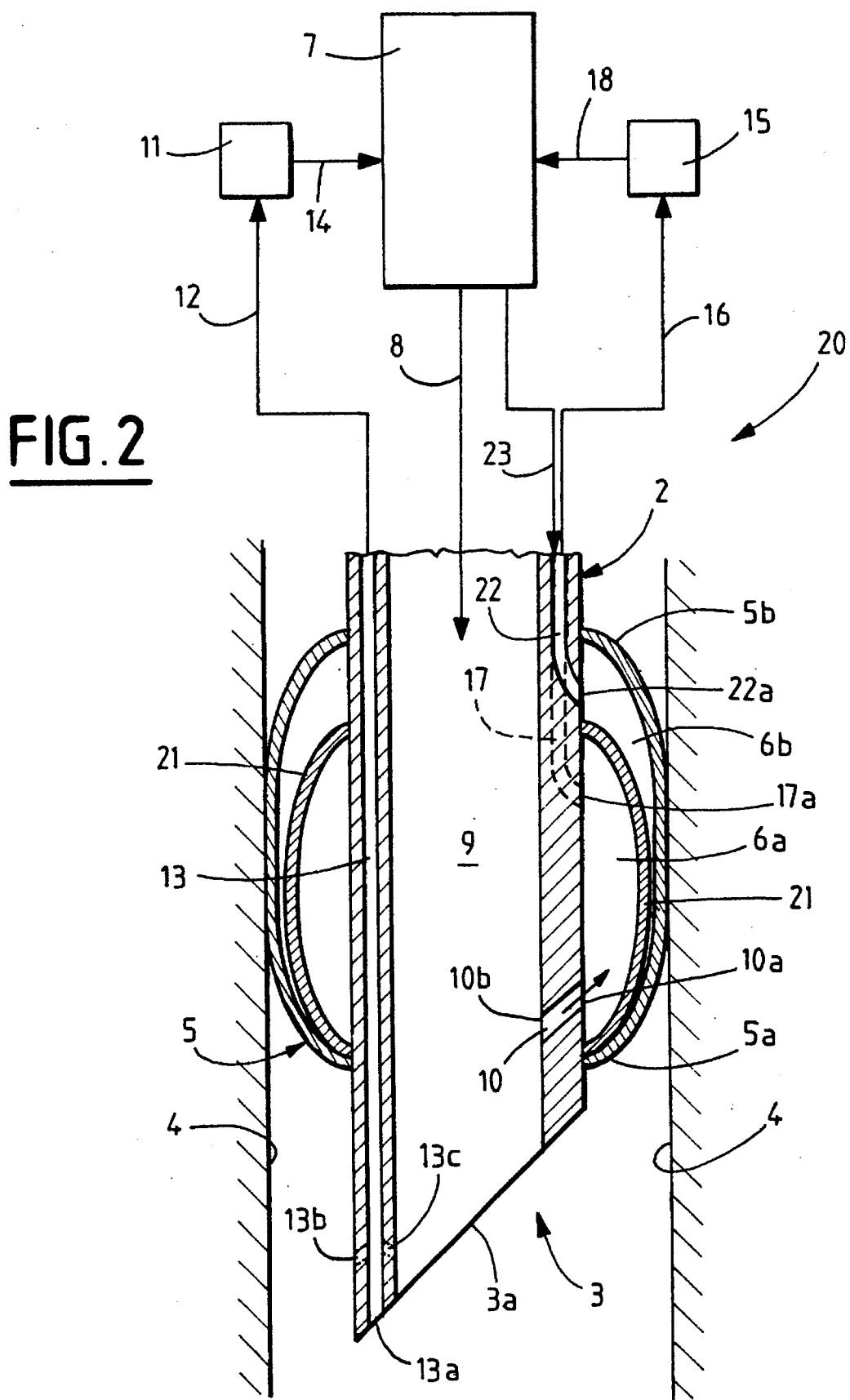

The variant embodiment 20 of the breathing-assistance tube of the invention as shown in FIG. 2 includes all of the elements 2 to 18 mentioned above with respect to the tube 1 of FIG. 1.

However, in this variant embodiment 20, the balloon 5 is internally subdivided into two closed cavities 6a and 6b by means of a flexible partition 21.

The cavity 6a is similar in practice to the cavity 6 of FIG. 1, and the ducts 10 and 17 open out therein in a manner similar to that described above.

A longitudinal capillary duct 22 opens out at 22a into the cavity 6b, the duct 22 being connected by a link 23 to the ventilator 7 and being received in the thickness of the wall of said tube.

Because of the link 23 it is thus possible to insert a gas under very low pressure into the cavity 6b, e.g. at a pressure of the order of 0.01 bars, so as to impart a small amount of permanent rigidity to the cavity 6b throughout the operation of the ventilator 7. Thus, during periods when the pressure of the breathing gas conveyed by the link 8 falls, only the cavity 6a deflates, so the balloon 5 retains a non-zero residual volume due to the cavity 6b being under low pressure. In contrast, when the breathing gas conveyed by the link 8 rises in pressure, only the cavity 6a (smaller than the cavity 6) is inflated for the purpose of providing sealing with the trachea 4.

It can thus be seen, that the partition 21, the duct 22, and the link 23 serve to synchronize changes in the pressure of the breathing gas travelling along the tube 2 with expansion and contraction movements of the balloon 5.

Figure 3:
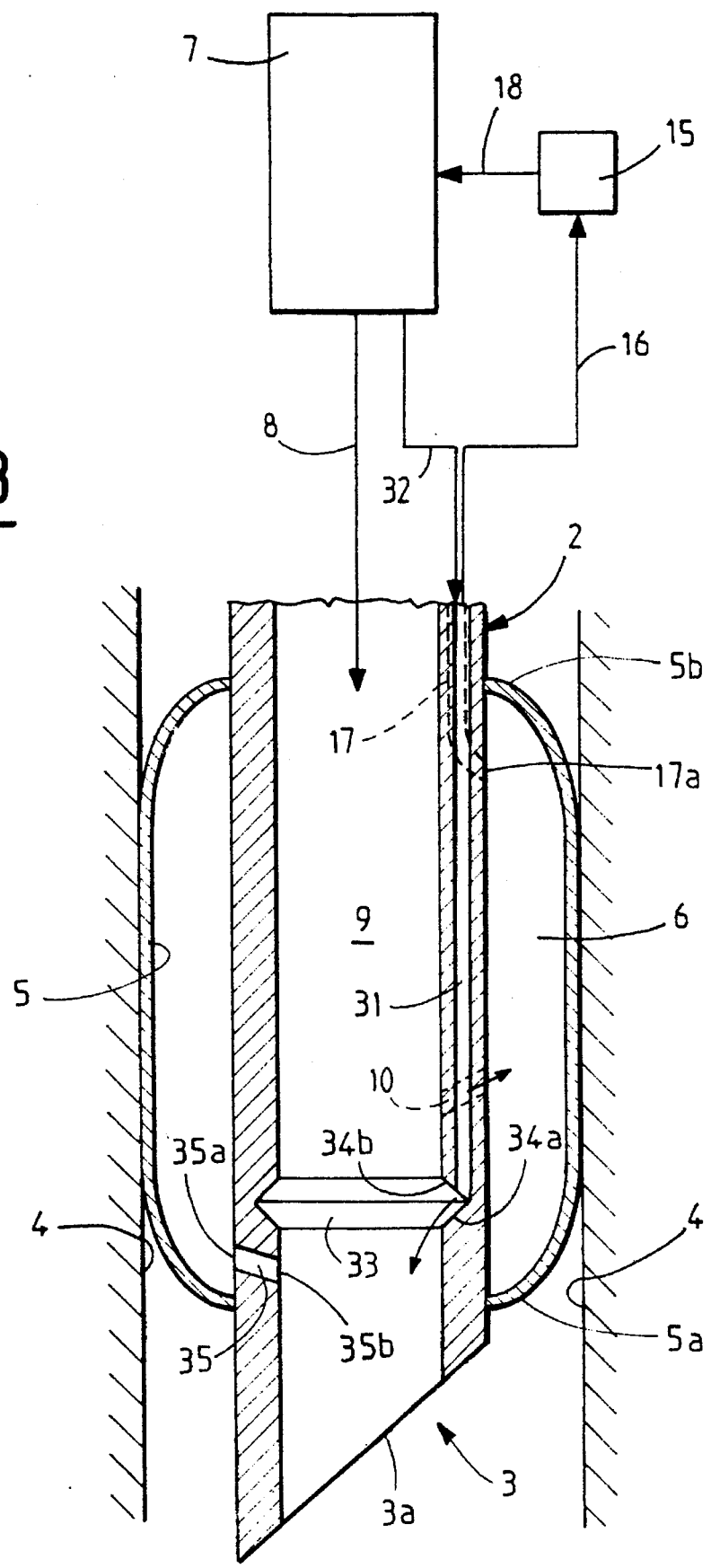

In the variant embodiment 30 of the breathing-assistance tube of the invention as shown in FIG. 3, there can be seen all of the elements 2 to 10 and 15 to 18 as described above and shown in FIG. 1.

Furthermore, in this embodiment, provision is made for at least one auxiliary duct 31 received in the thickness of the wall of the tube 2 and suitable for being connected at its proximal end to the ventilator 7 via a link 32. At its distal end, the duct 31 opens out into an annular recess 33 constituted by conical surfaces 34a and 34b that slope in opposite directions and that converge towards the axis of the tube 2. When the ventilator 7 applies breathing gas under pressure to the auxiliary duct 31 via the link 32, the jet of gas leaving the distal end of said duct 31 encounters the sloping face 34a which deflects it towards the axis of said tube 2. This gives rise to improved gas flow within the lumen 9 of the tube 2, thereby facilitating passage into the lungs of the patient of the breathing gas delivered to the tube 2 via the link 8.

The annular recess 33 is closer to the distal end face 3a than to the duct 10.

In addition, a duct 35 is formed in the thickness of the wall of the tube 2, which duct opens out at 35a to the inside 6 of the balloon 5 and at 35b to the inside of the tube 2 downstream from the annular recess 33 relative to the flow of insufflated breathing gas), and thus in the vicinity of the distal end face 3a.

Thus, if excess pressure should occur in the pulmonary passages of the patient, it is transmitted to the cavity 6 of the balloon 5 via the duct 35 and is then detected by the sensor 15 via the duct 17 and the link 16. The sensor 15 can then stop operation of the ventilator 7.

The variant embodiment 30 of FIG. 3 could naturally include a balloon 5 having two cavities 6a and 6b (the cavity 6a being connected via a link 23 to the ventilator 7, as explained above), as described above with reference to the embodiment 20 of FIG. 2. Under such circumstances, the ducts 10, 17, and 35 would open out into the cavity 6a, while the duct 22 would open out into the cavity (6b).

Naturally, it is possible to provide a plurality of ducts for the breathing-assistance tube of the present invention, each duct corresponding to one or more of the ducts 10, 17, 22, and/or 31. In any event, these various ducts are distributed around the axis of the tube 2 so as to avoid interfering with one another.

I claim:

1. A breathing assistance tube (2), having a lumen, having a wall having thickness, having a distal end (3) having a face, said distal end being designed to be inserted into a trachea (4) of a patient and which is provided with an inflatable balloon (5) having an inside, an outside and a cavity, said inflatable balloon being for providing sealing between said breathing-assistance tube and a trachea, and having a proximal end which is designed to be connected to means (7, 8) for conveying breathing gas to lungs of a patient via said tube, said breathing-assistance tube comprising:

(a) at least one communication duct (10) passing through the wall of said tube (2) and establishing communication (10) between the lumen (9) of said tube and the inside of said balloon (5);

(b) at least one first longitudinal duct (17) opening out into said balloon, said duct being designed to connect said cavity (6) to the exterior of a patient, wherein said inflatable balloon (5) is subdivided into a first and a second cavity (6a and 6b), said communication duct (10) and said first longitudinal duct (17) opening out into said first cavity (6a) and a second longitudinal duct (22) opening out into said second cavity (6b), the second longitudinal duct being suitable for connection to a source of gas.

2. The breathing-assistance tube (2) according to claim 1, wherein said first longitudinal duct (17) is provided in the thickness of the wall of said tube (2).

3. The breathing-assistance tube (2) according to claim 1, wherein said first longitudinal duct (17) is connected to a pressure sensor (15) suitable for monitoring the operation of said means (7, 8) delivering the breathing gas to the lungs of a patient.

4. The breathing-assistance tube (2) according to claim 1, wherein said first longitudinal duct (17) opens out (at point 17a) into the cavity (6a) of said balloon (5) in the vicinity of the proximal end (5b) of said balloon.

5. The breathing-assistance tube (2) according to claim 1, wherein said communication duct (10) is located in the vicinity of the distal end (5a) of the balloon (5).

6. The breathing-assistance tube (2) according to claim 1, wherein said communication duct (10) is inclined relative to said tube (2), the orifice (10b) through which said communication duct (10) opens out into the lumen (9) of said tube being closer to the distal end face (3a) thereof than is the orifice (10a) whereby said communication duct (10) opens into said balloon.

7. The breathing assistance tube (2) according to claim 1, including internal deflection means (33, 34a) for at least one jet of breathing gas conveyed by a third longitudinal duct (31), wherein said breathing-assistance tube includes another through duct (35) connecting said balloon (5) with the portion of said lumen (9) of said tube lying between said internal deflection means (33, 34a) and the distal end face (3a) of said tube.

8. The breathing-assistance tube (2) according to claim 7, wherein said other through duct (35) connecting said balloon (5) to the portion of said lumen (9) of said tube that lies between said internal deflection means (33, 34a) and the distal end face (3a) of said tube (2) opens out into said cavity (6a), along with said communication duct (10) and said first longitudinal duct (17).

9. The breathing-assistance tube (2) according to claim 7, wherein said third longitudinal duct (31) is provided in the thickness of the wall of said tube (2).

10. The breathing-assistance tube (2) according to claim 1, wherein said second longitudinal duct (22) is provided in the thickness of the wall of said tube (2).

* * * * *